United States Patent [19]

Peferoen et al.

[11] Patent Number: 5,304,697
[45] Date of Patent: Apr. 19, 1994

[54] PROCESS FOR UPGRADING A PARAFFINIC FEEDSTOCK

[75] Inventors: Danny G. R. Peferoen; Krijn P. de Jong; Jean-Pierre Gilson; Willem H. J. Stork; Swan T. Sie; Carolus M. A. M. Mesters, all of Amsterdam, Netherlands

[73] Assignee: Shell Oil Company, Houston, Tex.

[21] Appl. No.: 43,422

[22] Filed: Apr. 6, 1993

[30] Foreign Application Priority Data

Apr. 8, 1992 [EP] European Pat. Off. ........ 92201015.2

[51] Int. Cl.$^5$ ............................ C07C 2/62; C07C 2/58
[52] U.S. Cl. ...................................... 585/720; 585/722
[58] Field of Search ................................ 585/720, 722

[56] References Cited

U.S. PATENT DOCUMENTS

| | | | |
|---|---|---|---|
| 3,706,814 | 12/1972 | Kirsch et al. | 585/722 |
| 3,865,894 | 2/1975 | Kirsch et al. | 585/722 |
| 4,992,616 | 2/1991 | Chou et al. | 585/722 |
| 5,073,665 | 12/1991 | Child et al. | 585/722 |

FOREIGN PATENT DOCUMENTS 2631956A 12/1989 France.
3-246325 11/1991 Japan.

*Primary Examiner*—Asok Pal

[57] ABSTRACT

Process for upgrading a paraffinic feedstock which includes: a) supplying the feedstock and an olefins-containing stream at a paraffin to olefin volume ratio greater than 2 to a reactor containing a zeolite-beta catalyst; and b) removing the upgraded product; wherein the process is operated at an olefin conversion of at least 90 mol % in an external circulation reactor having an extent of external circulation of liquid reactor content expressed as $$\frac{\phi/vc + \phi/v}{\phi/v}$$

of greater than 2 wherein $\phi/v$ is the volumetric flow rate of feedstock and olefins-containing stream and $\phi/vc$ is the volumetric external circulation flow rate, and upgraded products produced by the process.

14 Claims, No Drawings

PROCESS FOR UPGRADING A PARAFFINIC FEEDSTOCK

FIELD OF THE INVENTION

The present invention relates to a process for upgrading a paraffinic feedstock. More specifically the invention relates to a process for alkylation of a paraffinic feedstock by the condensation of paraffins with olefins.

BACKGROUND OF THE INVENTION

Paraffins and olefins are the product of such methods as fluid catalytic cracking, MTBE etherification, or olefin isomerization. Production of highly branched hydrocarbons such as trimethylpentanes is important by virtue of their use as gasoline blending components high octane number. Traditional production of highly branched hydrocarbons is by condensation of isobutane with light olefins, usually butenes but sometimes mixtures of propene, butenes and possibly pentenes, using large quantities of conventional strong liquid acid catalysts, such as hydrofluoric or sulphuric acids. A mixture of immiscible acid and hydrocarbon is agitated to itiix the catalyst and reactant and refrigerated to control the highly exothermic reaction. By fine control of a complex interrelation of process variables, high quality alkylate production is maintained. The acid is recycled after use. It is desirable to use a process which is less hazardous and environmentally more acceptable.

Processes have been proposed to overcome these problems by using solid acids as catalysts. However paraffin-olefin condensation yields both desired alkylate and undesired oligomerization product. When catalyzing alkylation with solid acids it has been found tilat the selectivity for alkylate over oligomerization product is less than that obtained with liquid acids. Moreover, oligomerization products are thought to cause the observed progressive deactivation of the catalyst. Regeneration techniques are known for removing hydrocarbonaceous deposits from solid catalysts and restoring catalyst activity. Nevertheless, the known regeneration techniques are typically not totally satisfactory. One technique, for example, is raising the catalyst to elevated temperatures and oxidizing the deposits. For this method the alkylation must be interrupted and reactor conditions altered which causes lost production time.

In U.S. Pat. No. 3,706,814 a process is disclosed for alkylation of isoparaffins using acidic zeolite catalysts and supplying to the reactor paraffin and olefin in a volume ratio of from 15 to 30, the concentration of unreacted olefin in the reactor being maintained at less than 12 mole percent. Specifically the process is operated in a continuous stirred reactor using a zeolite Y catalyst. However, the experimental results in the '814 patent indicated severe deactivation occured even at low catalyst ages.

In the process of French patent No. 2,631,956, isobutane and butene are reacted over zeolite-beta catalyst in an upflow fixed bed reactor. Product analysis at 1 hour and 4 hours time on stream shows a decrease in the percentage olefin conversion level in the reactor with time on stream.

It would be advantageous to have an alkylation process which selectively yields highly branched alkylate at an acceptable rate for prolonged periods on stream.

SUMMARY OF THE INVENTION

The present invention provides a process for upgrading a paraffinic feedstock by:

a) supplying the feedstock and an olefins-containing stream at a paraffin to olefin volume ratio greater than 2 to a reactor containing a zeolite-beta catalyst; and, b) removing the upgraded product;

wherein the process is operated at an olefin conversion of at least 90 mol % in an external circulation reactor having an extent of external circulation of liquid reactor content expressed as $$\frac{\phi/vc + \phi/v}{\phi/v}$$

of greater than 2 wherein $\phi/v$ is the combined volumetric flow rate of feedstock and olefins-containing stream, and $\phi/vc$ is the volumetric external circulation flow rate.

By operation of a solid acid catalyzed alkylation process at a high extent of external circulation of liquid reactor content the rate of catalyst deactivation is significantly decreased. Furthermore such operation particularly beneficial selectivity for highly branched paraffins is achieved for the duration of the catalyst activity.

By the use of this process the alkylation activity of a zeolite beta-type catalyst is substantially improved.

DETAILED DESCRIPTION OF THE EMBODIMENTS

A. Feed and Product

Unless otherwise stated, "paraffin to olefin ratio" as used in this specification and appended claims means the quantity of paraffin feedstock per unit quantity of olefin introduced into the reactor, where each quantity is measured on a volume basis.

"Alkylate" as used in this specification and appended claims means a mixed condensation product of paraffin with olefin. "Oligomerization product" as used in this specification and appended claims means a condensation product of a plurality of olefin molecules.

Alkylate is characterized by a higher motor octane number (MON) than oligomerization product. Typically alkylate including highly branched paraffins with from about 5 to about 12 carbon atoms has a MON of 86 or above, for example, from about 90 to about 94. A corresponding oligomerization product of a mixture of paraffinic or olefinic hydrocarbons typically has a MON of less than 85, for example, from about 80 to about 82.

A preferred operation of the process of the invention is in the preparation of highly branched paraffins containing 5 to 12 carbon atoms, preferably containing from 5 to 9 or 12 carbon atoms, and most preferably trimethyl-butane, -pentane or -hexane. The process is applicable in the upgrading of a paraffinic feedstock including iso-paraffins having from 4 to 8 carbon atoms. The feedstock optionally includes isobutane, 2-methylbutane, 2,3-dimethylbutane, 3-methylhexane, or 2,4-dimethylhexane. The feedstock preferably is paraffinic and includes iso-paraffins having from 4 to 5 carbons. Feedstocks for the process of the invention also include iso-paraffin-containing fractions of oil conversion products such as naphtha fractions, and refined iso-paraffin feedstocks such as refined iso-butane. As mentioned above, it is convenient to isolate the iso-paraffin content of the effluent stream of liquid reactor products, for re-use as feedstock.

The olefin-containing stream used in the invention is typically in the form of a lower olefin-containing hydrocarbon which optionally contains additional non-olefinic hydrocarbons. Preferably the olefin-containing stream includes ethene, propene, iso-butene, 1-butene, 2-(cis or trans) butene, or pentene optionally diluted, for example, with propane, iso-butane, n-butane or pentanes.

REACTORS AND EXTERNAL CIRCULATION

Reactors for producing branched alkylates should include internal or external circulation of the reactor contents. "External circulation" of liquid reactor content as used in this specification and appended claims means that a portion of liquid reactor content is isolated from the remainder of the liquid reactor content and transported via transport means such as a conduit to re-enter the reactor. An external circulation means is optionally external to the reactor or wholly or partially surrounded by the reactor for substantially all or part of its length, for example, as a conduit means across the reactor includes a reactor inner wall or integral with the reactor outer wall. A high extent of external circulation of liquid reactor content is optionally attained in known reactor types such as solid phase fixed bed reactors or liquid phase continuous stirred tank reactors operated with external circulation along part or all of the length of the reactor and optionally operated with feed crossflow.

In the process of the invention the liquid reactor product consists essentially of upgraded product, that is, alkylate, and any unreacted paraffin. It is possible to externally circulate a part of the upgraded product since the alkylate therein appears to be essentially stable under the applied process conditions to further reaction in the presence of catalyst. The remainder of the upgraded product is fed to a separation unit such as a distillation column for separation of alkylate from unreacted paraffin. Unreacted paraffin is optionally reused as feedstock paraffin and is optionally fed back to the feedstock inlet by known means. The branched alkylates products are typically fed to a further process unit for conversion of the alkylates to other products.

A particular advantage of the invention is the use of upgraded product for external circulation without the need for an intermediate alkylate separation stage. Conventional means are used to regulate the rates of introduction of paraffin, olefin, the rate of removal of upgraded product and the rate of external circulation. Conventional means are used to divide off a portion of upgraded product for circulation. Such means preferably are of high throughput capacity and are physical separation means. Therefore conveniently upgraded product for external circulation is typically drawn from the reactor effluent in which case a T-junction with regulated flow is optionally included in the reactor outlet.

Excellent results are achieved with the process of the invention when operated in a single reactor. However, in a preferred embodiment, the process of the invention is operated in a cascade of reactors with split feed to each reactor and where lower volumetric external circulation flow rates are used. A cascade of reactors is optionally housed in a single unit or in separate units. Increased capacity is achieved by operation of a cascade of reactors in parallel. Up to ten reactors in series or parallel are optionally used, preferably up to eight reactors and most preferably five reactors. Feed supply to each operating bed of a multiple fixed bed downflow reactor optionally includes individual feed lines supplied from a central feed line. The conditions according to the process of the invention are attainable in other known reactor types.

Volumetric flow rates are determined in the reactor effluent and external recycle by known techniques. For example, such flow rates are determined by use of a rotameter, or by establishing the capacity of the recycle pump and the setting of the regulating flow valve to measure flow rate. Other methods include by use of an anemometer or pitot tube for measurement of differential pressure or by use of a mass flow meter together with density determination. Conventional apparatus and techniques are disclosed in "Chemical Engineer's Handbook" Perry and Chilton, McGraw-Hill, 1973, 5th ed. at 5-8 to 5-14.

C. OLEFIN CONVERSION AND RELATED PROCESS CONDITIONS

Olefin conversion is defined as the ratio of olefin consumed in the reactor to the olefin introduced to the reactor. At a high level of olefin conversion the desired alkylate product is obtained. High olefin conversion levels are achieved by use of appropriate olefin space velocities typically in excess of 0.01 kg/kg·h and high activity catalysts together with appropriate reactor temperature, composition and rate of introduction of paraffin and olefin and removal of upgraded product during the reaction. The level of olefin conversion is conveniently measured by applying gas chromatographic techniques to the effluent of the reactor. The preferred olefin conversion substantially throughout the reactor is at least 95 mol %, more preferably at least 98 mol % or at least 99 mol %. Most preferably olefin conversion is substantially complete, i.e., substantially 100 mol %.

The process is advantageously operated at an olefin space velocity at which at least 90 mol % olefin conversion is obtained. Olefin space velocity is defined as the weight of olefin introduced into the reactor per unit time per unit weight of catalyst in the reactor. A typical olefin space velocity lies is from about 0.01 kg/kg·h to about 10 kg/kg·h. The olefin space velocity is from 0.01 kg/kg·h to 10 kg/kg·h, preferably from 0.01 kg/kg·h to 5 kg/kg·h more preferably from 0.01 kg/kg·h to 0.5 kg/kg·h, and most preferably from 0.05 kg/kg·h to 0.10 kg/kg·h.

Operating conditions are selected as required whereby olefin space velocity is increased above the optimum for ease of operation at sacrifice of some catalyst life. Catalyst life is defined as the catalyst age at which deactivation is substantially complete. Catalyst age is defined as the weight olefin supplied to the reactor per the unit catalyst weight in the reactor. This is calculated as the product of olefin space velocity and time on stream. It has been found that the process of the invention is operable at high catalyst ages before full deactivation of the catalyst takes place. Operation beyond a catalyst life of 7 kg/kg and up to lives of the order of 15 kg/kg has been attained.

As a further advantage of the invention, operation at high olefin conversion levels in a reactor with external circulation according to the invention results in high alkylate yields with selectivity to highly branched alkylates throughout the progressive deactivation of the catalyst. Only at full deactivation has olefin breakthrough been observed. Thus, it is typically economical to operate the process for the full catalyst life.

D. Other Process Conditions

The alkylation reaction is preferably carried out under alkylation conditions including a temperature less than about 150° C., more preferably from about 60° C. to about 120° C. Reaction pressure is from about 1 atmosphere to about 40 atmospheres. Typically, the pressure is above the vapor pressure of the reactor contents so as to maintain the reaction in the liquid phase.

The process of the invention is operated at a paraffin to olefin volume ratio in excess of from about about 2 to about 20, preferably above 5, more preferably from about 10 to about 30, and most preferably from about 15 to about 30. A low paraffin to olefin volume ratio typically from about 2 to about 10 favors the formation of higher alkylates, such as isoparaffins containing 12 carbon atoms.

In preferred reactors the extent of external circulation of liquid reactor contents is greater than about 50. More preferably the external circulation is greater than about 60, for example, from about 75 to about 150 and most preferably from about 80 to about 120.

The process is advantageously operated by application of Advanced Process Control and optionally Online Optimization techniques using, respectively, multivariable dynamic and static models for the constraint control of selected process parameters. In a preferred operation of the process of the invention the alkylate obtained during operation is monitored and quality data together with the relevant operational process data are fed to an Advanced Process Control System. Real time solutions of the Advanced Process Controller are automatically fed back to a process implementation system and implemented in order to ensure the process parameters remain within operating constraints. Beneficial results are obtained by maintaining process parameters such as volumetric flow rates, temperature and olefin space velocity within the predetermined constraints.

E. The Catalyst

The catalyst used in the process of the invention is a zeolite-beta catalyst. This is any catalyst which conforms to the structural classification of a zeolite-beta, such as described in Newman, Treacy et al., Proc. R. Soc. London Ser. A 420, 375, (1988). The zeolitic catalyst is typically present on a support. For example, the catalyst further includes a refractory oxide that serves as binder material such as alumina, silica-alumina, magnesia, titania, zirconia and mixtures thereof. Alumina is specially preferred. The weight ratio of refractory oxide to zeolite is typically from about 10:90 to about 90:10, preferably from about 50:50 to about 15:85.

The catalyst is used in the form of pellets, which are preferably from about 0.1 mm to about 1 mm in size. Typically the pellets are crystals of zeolite-beta having a size of from 200 Ångstroms to 2000 Ångstroms, preferably of from 200 Ångstroms to 1000 Ångstroms. Crystal size is measured by known techniques such as transmission electron microscopy, or thickness surface area characterization as described in B. C. Lippens and J. H. deBoer, J. Catal., 4, 319 (1965) and in J. Lynch, F. Raatz and Ch. Delalande, Studies in Surf. Science and Catalysis, Vol. 39, pp. 547-557. With the above described catalyst, advantageous catalyst activity and intrapellet diffusion are thereby achieved.

Preferably the process of the invention is operated with a highly acidic zeolite-beta catalyst. The acid site density is determined by titration, for example, with butylamine, or by NMR or IR techniques. A high acid site density is beneficial in prolonging the catalyst age prior to deactivation. A highly acidic zeolite-beta catalyst is advantageously used in the process of the invention at high olefin space velocities and results in increased rate of production of alkylate. Although the acid strength of sites can be determined as such, to assist in choosing an appropriate catalyst is convenient to use known techniques for comparing catalyst acid site strengths as given, for example, in relation to zeolite catalysts in van Bekkum, Flanigen, Jansen, and Elsevier, *Introduction to Zeolite Science and Practice* 268-78 (1991).

It is desired to increase the potential catalyst life prior to use by increasing the availability of acid sites at which reaction take place. In addition to, or as an alteranative to, choosing a highly acidic catalyst, the catalyst is optionally treated to increase the acid site density by techniques known in the art. A zeolitic catalyst is treated, for example, with an alkali wash such as sodium hydroxide to redistribute the alumina within the catalyst, decreasing the silica-alumina lattice ratio. Alternatively, a high alumina content zeolite-beta is synthesized for use.

By the process of the invention it is possible to operate at an acceptable selectivity, i.e., obtaining an acceptable alkylate yield for the duration of the time on stream. By this means the catalyst alkylation activity is upheld throughout partial deactivation and until full deactivation of all sites has occurred, at which point olefin breakthrough is observed. Breakthrough is conveniently indicated by gas chromatography. Hence for the duration of time on stream it would appear that undesired oligomerization product remains associated with the acid sites of the catalyst and is not detected in the product.

F. Catalyst Regeneration

Regeneration of the catalyst is carried out by techniques known in the art for desorbing hydrocarbonaceous deposits from acid sites, such as oxidative regeneration at elevated temperature in an oxygen-rich atmosphere. The process of the invention is characterized by increased efficiency in cases in which the regeneration rate is greater than the deactivation rate. Hence techniques which increase the regeneration rate are of particular advantage in the process.

Regeneration is optionally carried out continuously. For example, one or more beds in a parallel or series multiple fixed bed downflow reactor are operated as desired in reaction or in regeneration mode. Alternatively, fresh or regenerated catalyst is continuously added to an independent reactor or each of a cascade of reactors simultaneously with continuous catalyst withdrawal from the reactor and the withdrawn catalyst passed to a regeneration reactor.

G. Start-up and Feed Nozzles

Preferably the reactor is started up in such a manner as to control initial contact of the catalyst with olefin feed. One method of start-up is where the reactor is first charged with paraffinic feedstock. An external circulation of liquid reactor contents is fed back to the fresh feed stream and an olefins-containing stream is subsequently continuously charged with the paraffinic feedstock at an olefin space velocity such that conversion is maintained in excess of 90 mol %. The feedstock and olefins stream are advantageously charged via a plurality of inlet ports, for example, in cross-flow configuration.

The use of nozzles to charge the reactor advantageously provides improved dispersion of charge at the site of introduction. Suitable nozzles are those known for use in alkylation reactions using hydrogen fluoride as catalyst and nozzles known for dispersion of feed in stirred tank reactors and fixed catalyst beds. In the operation of a cascade of reactors, recycle can be used whereby the effluent of one reactor is externally recycled to previous reactors.

The process is now illustrated by way of a non-limiting embodiment.

ILLUSTRATED EMBODIMENT

A. An Embodiment of the Invention

A single fixed bed reactor with one external recycle containing zeolite-beta catalyst having pellet size of 0.1 mm and a silica to alumina ratio of 12.7, was charged with liquid isobutane feedstock. The reactor and its contents were heated and the reaction temperature was maintained at from about 80° C. to about 90° C. Introduction of isobutane was maintained simultaneously with drawing off of liquid reactor contents from below the bed and a part thereof externally circulated to the reactor at an extent of recycle of 100. 2-Butene was continuously added with isobutane feedstock at a paraffin to olefin volume ratio of 30 and an olefin space velocity of 0.08 kg/kg·h. Alkylate was produced for 100 hours. Olefin conversion was greater than 99 mol %, i.e., substantially complete. The results are given in the Table below measured over two sampling periods at 8 and 16 hours on stream. Deactivation occurred at catalyst life of 8 kg/kg.

Yield of the essentially paraffinic C5+ product was measured as 200% by weight on olefin.

TABLE

| Product[1] | Yield (%) obtained at sampling periods | |
|---|---|---|
| | 8 h | 16 h |
| C5/C5+ | 4 | 3 |
| C6/C5+ | 8 | 8 |
| C7/C5+ | 4 | 8 |
| C8/C5+ | 73 | 63 |
| C9+/C5+ | + 11 | + 18 |
| Total | 100 | 100 |
| TMP/C8 | 75 | 80 |

TMP is trimethylpentanes. Yields are given as % of total yield in percent of C5+ or C8 as indicated.
[1]The product is expressed as a percentage where the product is the compound in the numerator and the percent is obtained by dividing the total yield of the product by the total yield of either C5+ or C8, as indicated, in the denominator and then multiplying by 100.

[1]The product is expressed as a percentage where the product is the compound in the numerator and the percent is obtained by dividing the total yield of the product by the total yield of either C5+ or C8, as indicated, in the denominator and then multiplying by 100.

B. Comparative Example Not of the Invention

The above experiment was repeated except that no external recycle was used. Since the catalyst deactivated very rapidly no alkylate was detected in the reactor of effluent.

What is claimed is:

1. An alkylation process for a paraffinic feedstock comprising
   a) supplying the feedstock and an olefins-containing stream at a paraffin to olefin volume ratio greater than 2 to a reactor containing a zeolite-beta catalyst and
   b) removing the product comprising alkylate, wherein the process is operated at an olefin conversion of at least 90 mol % in an external circulation reactor having an extent of external circulation of liquid reactor content expressed as $$\frac{\phi/vc + \phi/v}{\phi/v}$$

of greater than 50 wherein $\phi/v$ is the volumetric flow rate of feedstock and olefins-containing stream and $\phi/vc$ is the volumetric external circulation flow rate and wherein said catalyst has a catalyst life in excess of 7 kg/kg.

2. The process according to claim 1 operated at olefin conversion of at least 95 mol %.

3. The process according to claim 2 wherein the extent of external circulation is greater than 60.

4. The process according to claim 2 wherein the reactor is first charged with paraffinic feedstock, an external circulation of liquid reactor contents is then fed back to the fresh feed stream and an olefins-containing stream is subsequently continuously charged with the paraffinic feedstock at an olefin space velocity such that conversion is maintained in excess of 90 mol %.

5. The process according to claim 4 wherein the olefin space velocity is from about 0.01 kg/kg·h to about 10 kg/kg·h.

6. The process according to claim 2 wherein the paraffin to olefin volume ratio is greater than 10.

7. The process according to claim 5 wherein said catalyst has a catalyst life in excess of 7 kg/kg.

8. The process according to claim 7 further comprising at least two reactors in series.

9. The process according to claim 8 wherein one or more reactors are operated in catalyst regeneration mode.

10. The process according to claim 7 wherein the reactor temperature is less than about 150° C.

11. The process according to claim 10 wherein the zeolite is in the form of crystals of size from about 200 Ångstroms to about 2000 Ångstroms.

12. The process according to claim 11 wherein the catalyst is in the form of pellets of size from about 0.1 mm to about 1 mm.

13. The process according to claim 11 wherein the catalyst has been treated to increase the acid site density.

14. An alkylation process for a paraffinic feedstock comprising
   a) supplying the feedstock and an olefins-containing stream at a paraffin to olefin volume ratio greater than 10 to a reactor at a temperature of less than about 150° C. containing a pellet-shaped zeolite-beta catalyst of pellet size from about 0.1 mm to about 1 mm and
   b) removing the product comprising alkylate; wherein the process is operated at an olefin conversion of at least 98 mol % in an external circulation reactor having an extent of external circulation of liquid reactor content expressed as $$\frac{\phi/vc + \phi/v}{\phi/v}$$

of from about 80 to about 120 wherein $\phi/v$ is the volumetric flow rate of feedstock and olefins-containing stream and $\phi/vc$ is the volumetric external circulation flow rate and wherein said catalyst has a catalyst life in excess of 7 kg/kg.

* * * * *